United States Patent
Koseoglu et al.

(10) Patent No.: US 11,874,258 B2
(45) Date of Patent: Jan. 16, 2024

(54) SYSTEM AND METHOD OF CHARACTERIZING CRUDE OIL BY GEL PERMEATION CHROMATOGRAPHY (GPC)

(71) Applicant: Saudi Arabian Oil Company, Dhahran (SA)

(72) Inventors: Omer Refa Koseoglu, Dhahran (SA); Saroj Kumar Panda, Dhahran (SA); Hendrik Muller, Dhahran (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 1498 days.

(21) Appl. No.: 16/157,222

(22) Filed: Oct. 11, 2018

(65) Prior Publication Data

US 2020/0116683 A1 Apr. 16, 2020

(51) Int. Cl.
- *G01N 30/86* (2006.01)
- *G01N 33/28* (2006.01)
- *G01N 30/02* (2006.01)

(52) U.S. Cl.
CPC ..... *G01N 30/8675* (2013.01); *G01N 30/8631* (2013.01); *G01N 33/2823* (2013.01); *G01N 33/2829* (2013.01); *G01N 2030/027* (2013.01)

(58) Field of Classification Search
CPC ........... G01N 30/8631; G01N 30/8675; G01N 33/2823; G01N 33/2829; G01N 2030/027
See application file for complete search history.

(56) References Cited

U.S. PATENT DOCUMENTS

| | | | | |
|---|---|---|---|---|
| 9,816,919 B2* | 11/2017 | Koseoglu | ........... | G01N 33/2823 |
| 10,048,194 B2* | 8/2018 | Koseoglu | ........... | G01N 33/2811 |
| 10,401,344 B2* | 9/2019 | Koseoglu | ........... | G01N 33/2823 |
| 10,527,546 B2* | 1/2020 | Koseoglu | ........... | G01N 21/6402 |
| 10,571,452 B2* | 2/2020 | Koseoglu | ........... | G01N 33/2811 |
| 10,684,239 B2* | 6/2020 | Koseoglu | ........... | G01R 33/4625 |
| 10,725,013 B2* | 7/2020 | Koseoglu | ........... | G01N 33/2823 |
| 10,928,375 B2* | 2/2021 | Al-Hajji | ................. | G01N 33/30 |
| 10,942,160 B2* | 3/2021 | Koseoglu | ........... | G01N 33/2841 |
| 11,022,588 B2* | 6/2021 | Koseoglu | ............... | G01N 30/88 |
| 11,320,413 B1* | 5/2022 | Koseoglu | ........... | H01J 49/0036 |
| 2015/0106027 A1* | 4/2015 | Koseoglu | ............... | G01R 33/46 |
| | | | | 702/23 |
| 2015/0106029 A1* | 4/2015 | Koseoglu | ............... | G01N 30/88 |
| | | | | 702/23 |
| 2016/0195481 A1* | 7/2016 | Koseoglu | ........... | G01N 25/4833 |
| | | | | 374/14 |
| 2016/0195507 A1* | 7/2016 | Koseoglu | ........... | G01N 33/2823 |
| | | | | 250/301 |

(Continued)

FOREIGN PATENT DOCUMENTS

WO 2016111989 A1 7/2016

OTHER PUBLICATIONS

Stout et al. "Separation and Gel Permeation Analysis of Natural Emulsion Stabilizers," SPE-1921 (Year: 1968).*

(Continued)

*Primary Examiner* — John Fitzgerald (74) *Attorney, Agent, or Firm* — Leason Ellis LLP (57) ABSTRACT

A system and a method are provided for calculating the cetane number, pour point, cloud point, aniline point, and/or octane number of a crude oil and its fractions from the density and gel permeation chromatography data of a sample of the crude oil.

14 Claims, 5 Drawing Sheets

(56) References Cited

U.S. PATENT DOCUMENTS

| | | | |
|---|---|---|---|
| 2016/0195508 A1* | 7/2016 | Al-Hajji | G01N 33/2811 250/206 |
| 2017/0363591 A1* | 12/2017 | Koseoglu | G01N 30/88 |
| 2017/0363603 A1* | 12/2017 | Koseoglu | G01N 33/2829 |
| 2020/0072812 A1* | 3/2020 | Al-Hajji | G01N 33/2811 |
| 2020/0264156 A1* | 8/2020 | Koseoglu | G01N 21/3577 |

OTHER PUBLICATIONS

Sugiyama et al. "Construction of Digital Oil for Investigation of Crude Oil Properties at Different Thermodynamic Conditions," IPTC-18779-MS (Year: 2016).*

International Search Report and Written Opinion for related international application PCT/2019/052831, dated Jan. 3, 2020 (12 pages).

"GPC Characterization for Assessing Compatibility Problems with Heavy Fuel Oils," Fuel Processing Technology, 9 (1984), p. 189-201.

"Software Releases," Computer Methods and Programs in Biomedicine 22 (1986), p. 345-347.

* cited by examiner

SYSTEM AND METHOD OF CHARACTERIZING CRUDE OIL BY GEL PERMEATION CHROMATOGRAPHY (GPC)

FIELD OF THE INVENTION

This invention relates to a system and method for the evaluation of samples of crude oil by gel permeation chromatography.

BACKGROUND OF THE INVENTION

Crude oil originates from the decomposition and transformation of aquatic, mainly marine, living organisms and/or land plants that became buried under successive layers of mud and silt some 15-500 million years ago. They are essentially very complex mixtures of many thousands of different hydrocarbons. Depending on the source, the oil predominantly contains various proportions of straight and branched-chain paraffins, cycloparaffins, and naphthenic, aromatic, and polynuclear aromatic hydrocarbons. These hydrocarbons can be gaseous, liquid, or solid under normal conditions of temperature and pressure, depending on the number and arrangement of carbon atoms in the molecules.

Crude oils vary widely in their physical and chemical properties from one geographical region to another and from field to field. Crude oils are usually classified into three groups according to the nature of the hydrocarbons they contain: paraffinic, naphthenic, asphaltic, and their mixtures. The differences are due to the different proportions of the various molecular types and sizes. One crude oil can contain mostly paraffins, another mostly naphthenes. Whether paraffinic or naphthenic, one can contain a large quantity of lighter hydrocarbons and be mobile or contain dissolved gases; another can consist mainly of heavier hydrocarbons and be highly viscous, with little or no dissolved gas. Crude oils can also include heteroatoms containing sulfur, nitrogen, nickel, vanadium and other elements in quantities that impact the refinery processing of the crude oil fractions. Light crude oils or condensates can contain sulfur in concentrations as low as 0.01 W %; in contrast, heavy crude oils can contain as much as 5-6 W %. Similarly, the nitrogen content of crude oils can range from 0.001-1.0 W %.

The nature of the crude oil governs, to a certain extent, the nature of the products that can be manufactured from it and their suitability for special applications. A naphthenic crude oil will be more suitable for the production of asphaltic bitumen, a paraffinic crude oil for wax. A naphthenic crude oil, and even more so an aromatic one, will yield lubricating oils with viscosities that are sensitive to temperature. However, with modern refining methods there is greater flexibility in the use of various crude oils to produce many desired type of products.

A crude oil assay is a traditional method of determining the nature of crude oils for benchmarking purposes. Crude oils are subjected to true boiling point (TBP) distillations and fractionations to provide different boiling point fractions. The crude oil distillations are carried out using the American Standard Testing Association (ASTM) Method D 2892. The common fractions and their nominal boiling points are given in Table 1.

TABLE 1

| Fraction | Boiling Point, ° C. |
|---|---|
| Methane | −161.5 |
| Ethane | −88.6 |

TABLE 1-continued

| Fraction | Boiling Point, ° C. |
|---|---|
| Propane | −42.1 |
| Butanes | −6.0 |
| Light Naphtha | 36-90 |
| Mid Naphtha | 90-160 |
| Heavy Naphtha | 160-205 |
| Light gas Oil | 205-260 |
| Mid Gas Oil | 260-315 |
| Heavy gas Oil | 315-370 |
| Light Vacuum Gas Oil | 370-430 |
| Mid Vacuum Gas Oil | 430-480 |
| Heavy vacuum gas oil | 480-565 |
| Vacuum Residue | 565+ |

The yields, composition, physical and indicative properties of these crude oil fractions, where applicable, are then determined during the crude assay work-up calculations. Typical compositional and property information obtained from a crude oil assay is given in Table 2.

TABLE 2

| Property | Unit | Property Type | Fraction |
|---|---|---|---|
| Yield Weight and Volume % | W % | Yield | All |
| API Gravity | ° | Physical | All |
| Viscosity Kinematic @ 38° C. | ° | Physical | Fraction boiling > 250° C. |
| Refractive Index @ 20° C. | Unitless | Physical | Fraction boiling < 400° C. |
| Sulfur | W % | Composition | All |
| Mercaptan Sulfur, W % | W % | Composition | Fraction boiling < 250° C. |
| Nickel | ppmw | Composition | Fraction boiling > 400° C. |
| Nitrogen | ppmw | Composition | All |
| Flash Point, COC | ° C. | Indicative | All |
| Cloud Point | ° C. | Indicative | Fraction boiling > 250° C. |
| Pour Point, (Upper) | ° C. | Indicative | Fraction boiling > 250° C. |
| Freezing Point | ° C. | Indicative | Fraction boiling > 250° C. |
| Micro Carbon Residue | W % | Indicative | Fraction boiling > 300° C. |
| Smoke Point, mm | mm | Indicative | Fraction boiling between 150-250° C. |
| Octane Number | Unitless | Indicative | Fraction boiling < 250° C. |
| Cetane Index | Unitless | Indicative | Fraction boiling between 150-400° C. |
| Aniline Point | ° C. | Indicative | Fraction boiling < 520° C. |

Due to the number of distillation cuts and the number of analyses involved, the crude oil assay work-up is both costly and time consuming.

In a typical refinery, crude oil is first fractionated in the atmospheric distillation column to separate sour gas and light hydrocarbons, including methane, ethane, propane, butanes and hydrogen sulfide, naphtha (36-180° C.), kerosene (180-240° C.), gas oil (240-370° C.) and atmospheric residue (>370° C.). The atmospheric residue from the atmospheric distillation column is either used as fuel oil or sent to a vacuum distillation unit, depending on the configuration of the refinery. The principal products obtained from vacuum distillation are vacuum gas oil, comprising hydrocarbons boiling in the range 370-520° C., and vacuum residue, comprising hydrocarbons boiling above 520° C. Crude assay data is conventionally obtained from individual analysis of these cuts to help refiners to understand the general composition of the crude oil fractions and properties so that the fractions can be processed most efficiently and effectively in an appropriate refining unit. Indicative properties are used to determine the engine/fuel performance or usability or flow characteristic or composition. A summary of the indicative properties and their determination methods with description is given below.

The cetane number of diesel fuel oil, determined by the ASTM D613 method, provides a measure of the ignition quality of diesel fuel; as determined in a standard single cylinder test engine; which measures ignition delay compared to primary reference fuels. The higher the cetane number; the easier the high-speed; direct-injection engine will start; and the less white smoking and diesel knock after start-up are. The cetane number of a diesel fuel oil is determined by comparing its combustion characteristics in a test engine with those for blends of reference fuels of known cetane number under standard operating conditions. This is accomplished using the bracketing hand wheel procedure which varies the compression ratio (hand wheel reading) for the sample and each of the two bracketing reference fuels to obtain a specific ignition delay, thus permitting interpolation of cetane number in terms of hand wheel reading.

The cloud point, determined by the ASTM D2500 method, is the temperature at which a cloud of wax crystals appears when a lubricant or distillate fuel is cooled under standard conditions. Cloud point indicates the tendency of the material to plug filters or small orifices under cold weather conditions. The specimen is cooled at a specified rate and examined periodically. The temperature at which cloud is first observed at the bottom of the test jar is recorded as the cloud point. This test method covers only petroleum products and biodiesel fuels that are transparent in 40 mm thick layers, and with a cloud point below 49° C.

The pour point of petroleum products, determined by the ASTM D97 method, is an indicator of the ability of oil or distillate fuel to flow at cold operating temperatures. It is the lowest temperature at which the fluid will flow when cooled under prescribed conditions. After preliminary heating, the sample is cooled at a specified rate and examined at intervals of 3° C. for flow characteristics. The lowest temperature at which movement of the specimen is observed is recorded as the pour point.

The aniline point, determined by the ASTM D611 method, is the lowest temperature at which equal volumes of aniline and hydrocarbon fuel or lubricant base stock are completely miscible. A measure of the aromatic content of a hydrocarbon blend is used to predict the solvency of a base stock or the cetane number of a distillate fuel. Specified volumes of aniline and sample, or aniline and sample plus n-heptane, are placed in a tube and mixed mechanically. The mixture is heated at a controlled rate until the two phases become miscible. The mixture is then cooled at a controlled rate and the temperature at which two separate phases are again formed is recorded as the aniline point or mixed aniline point.

The octane number, determined by the ASTM D2699 or D2700 methods, is a measure of a fuel's ability to prevent detonation in a spark ignition engine. Measured in a standard single-cylinder; variable-compression-ratio engine by comparison with primary reference fuels. Under mild conditions, the engine measures research octane number (RON), while under severe conditions, the engine measures motor octane number (MON). Where the law requires posting of octane numbers on dispensing pumps, the antiknock index (AKI) is used. This is the arithmetic average of RON and MON, (R+M)/2. It approximates the road octane number, which is a measure of how an average car responds to the fuel.

To determine these properties of gas oil or naphtha fractions conventionally, these fractions have to be distilled from the crude oil and then measured/identified using various analytical methods that are laborious, costly and time-consuming.

This invention discloses a system and method in which gel permeation chromatography analysis is employed to disclose physical and indicative properties (i.e., cetane number, pour point, cloud point, and aniline point) of gas oil fraction of crude oils, as well as the octane number of the naphtha fraction. The invention provides insight into the gas oil and naphtha properties without fractionation/distillation (crude oil assays) and will help producers, refiners, and marketers to benchmark the oil quality and, as a result, valuate the oils without going thru costly and time-consuming crude oil assays. Whereas a conventional crude oil assay method could take up to two months and cost $50,000, this invention provides results within one hour.

New rapid, and direct methods to help better understand crude oil compositions and properties from analysis of whole crude oil will save producers, marketers, refiners and/or other crude oil users substantial expense, effort and time. Therefore, a need exists for an improved system and method for determining indicative properties of crude oil fractions from different sources.

SUMMARY OF THE INVENTION

Systems and methods for determining one or more indicative properties of a hydrocarbon sample are presented. Indicative properties in a crude oil sample (e.g., cetane number, pour point, cloud point and aniline point) of a gas oil fraction, and octane number of a naphtha fraction, are assigned as a function of density and gel permeation chromatography data of a crude oil sample. The indicative properties provide information about the gas oil and naphtha properties without fractionation/distillation (crude oil assays) and help producers, refiners, and marketers to benchmark the oil quality and, as a result, valuate the oils without performing the customary extensive and time-consuming crude oil assays.

BRIEF DESCRIPTION OF THE DRAWINGS

Further advantages and features of the present invention will become apparent from the following detailed description of the invention when considered with reference to the accompanying drawings in which.

DETAILED DESCRIPTION OF INVENTION

A system and a method are provided for determining one or more indicative properties of a hydrocarbon sample. Indicative properties (e.g., cetane number, pour point, cloud point, and aniline point) of a gas oil fraction and octane number of a naphtha fraction in a crude oil sample are assigned as a function of the density and gel permeation chromatography measurement of the crude oil sample. The indicative properties provide information about the gas oil and naphtha properties without fractionation/distillation (crude oil assays) and help producers, refiners, and marketers to benchmark the oil quality and, as a result, valuate the oils without performing the customary extensive and time-consuming crude oil assays.

The systems and methods are applicable for naturally occurring hydrocarbons derived from crude oils, bitumens, heavy oils, shale oils and from refinery process units including hydrotreating, hydroprocessing, fluid catalytic cracking, coking, and visbreaking or coal liquefaction.

In the system and method herein, gel permeation data is obtained by a suitable known or to-be-developed process.

Gel permeation chromatography (GPC) is a technique commonly used to separate compounds based on the size in solution. Recently, a method using GPC has been used to determine the boiling point distribution of high boiling petroleum fractions (Grzegorz Boczkaj, Andrzej Przyjazny, Marian Kaminski "Size-exclusion chromatography for the determination of the boiling point distribution of high-boiling petroleum fractions" J. Sep. Sci. 2015, 38, 741-748.). The method was compared with ASTM D2887 and was found to be superior for the determination of final boiling point values of high boiling mixtures up to about 550° C. We further improved the GPC method to be suitable for crude oils of various origins. The detailed description of the GPC method is shown in Table 3.

TABLE 3

Sample concentration and GPC conditions.

| Sample concentration | 0.05 g/mL in tetrahydrofuran |
|---|---|
| Flow rate | 1 mL/min |
| Detector | Refractive Index detector |
| Injection volume | 100 µL |
| Run time | 37 minutes |
| Mobile phase | Tetrahydrofuran |
| Column | Three columns in series (300 × 7.8 mm, 5 µm): Phenogel 1000 Å, 100 Å and 50 Å |
| Column oven temperature | 30° C. |

The indicative properties (e.g., the cetane number, pour point, cloud point and aniline point) of the gas oil fraction, e.g., boiling in the range of 150-400° C. and in certain embodiments in the range of 180-370° C., and the octane number of the naphtha fraction, e.g., boiling above 250° C. can be assigned as a function of the density and the GPC Index of whole crude oil (GPCI).

Figure 1:
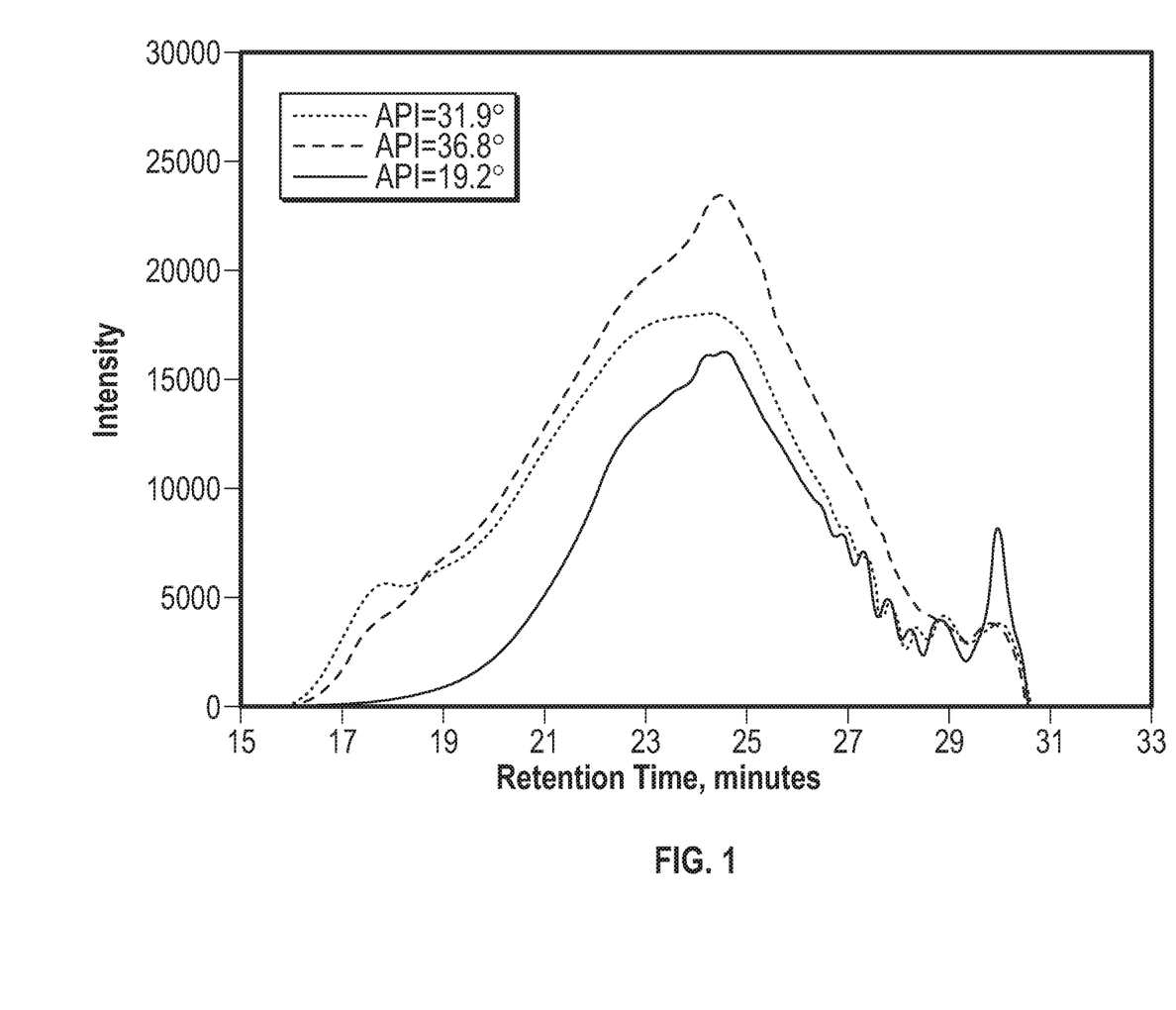
FIG. 1 is a graphic plot of gel permeation chromatography data obtained for three types of crude oils.
Figure 2:
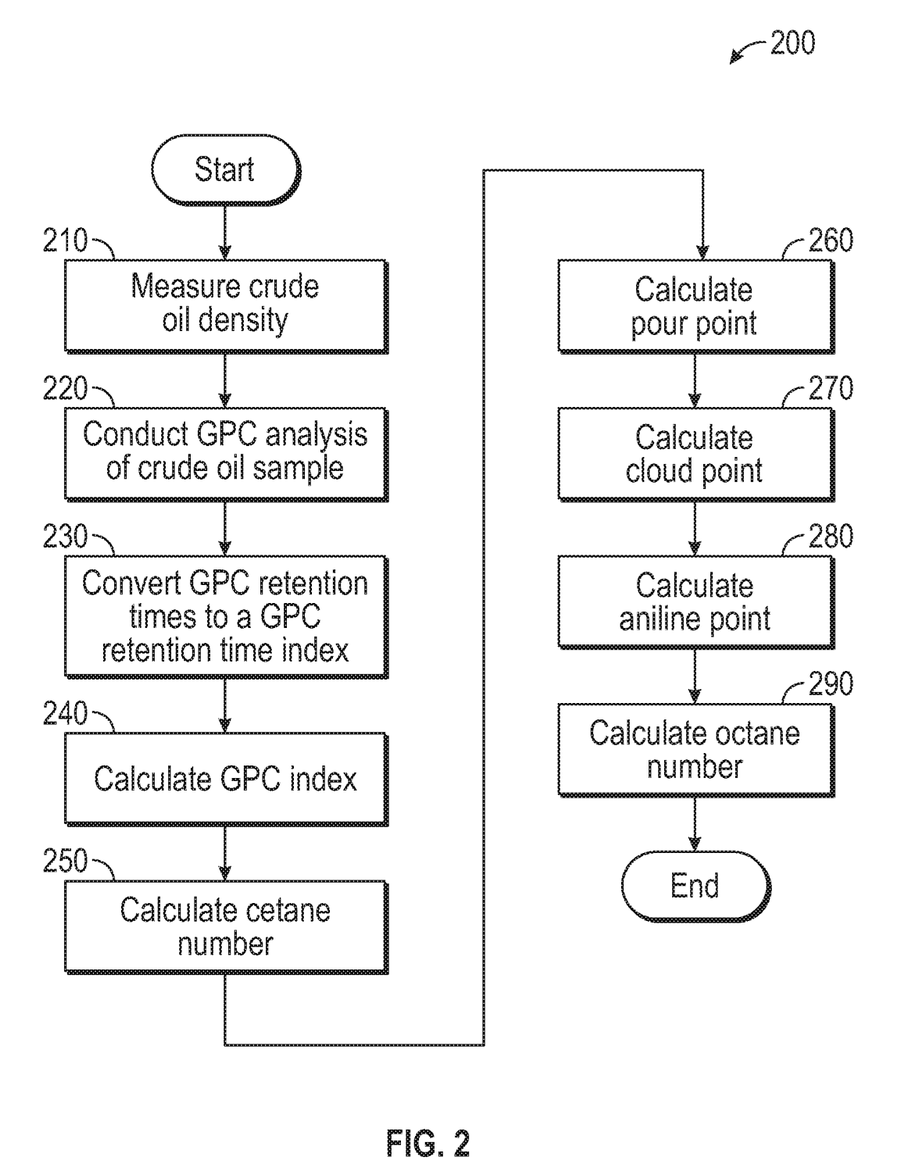
FIG. 2 is a process flow diagram of steps of a method in which an embodiment of the invention is implemented.

FIG. 2 shows a process flowchart of steps in a method according to one embodiment herein that occur after gel permeation chromatography is completed and the results are tabulated. In step 210, gel permeation chromatography is completed. In step 220, GPC retention times of the gel permeation chromatography data are converted to a GPC retention time index, GPC-RTI, which is converted to molecular weight. In step 230, a GPC index (GPCI) is calculated from gel permeation chromatography data and the molecular weight. In step 240, the crude oil density is measured. In step 250, the cetane number is calculated from the GPC index and the density. In step 260, the pour point is calculated from the GPC index and the density. In step 270, the cloud point is calculated from the GPC index and the density. In step 280, the aniline point is calculated from the GPC index and the density. In step 290, the octane number is calculated from the GPC index and the density. Steps 250-290 can be performed in parallel or in any order. In certain embodiments, only one or more or steps 250, 260, 270, 280, 290 are carried out.

That is, $$\text{Indicative Property} = f(\text{density}_{crude\ oil}, \text{GPCI}_{crude\ oil}) \quad (1)$$

In step 210, the density of the crude oil sample is measured.

In step 220, the GPC analysis is conducted.

In step 230, to calculate GPC Index (GPCI), the GPC retention times are first converted to a GPC retention time index GPC-RTI as shown below:

$$\text{GPC-RTI} = 100*(\text{FP}-\text{RT})/(\text{FP}-\text{FE}) \quad (2)$$

Where:
FP: full permeation time in minutes (retention time for solvent), e.g., 30.67 min for the example chromatographic apparatus
RT: retention time at any point in minutes
FE: full exclusion time in minutes (retention time for material that is fully excluded from the stationary phase pores), e.g., 14.05 min for the example chromatographic apparatus GPC-RTI is then converted to molecular weight as per the equation 3:

$$\text{MW} = 16.309*\text{GPC-RTI} - 147.734 \quad (3)$$

The molecular weight correlation of a crude oil with its GPC-RTI was obtained using fractionation of the crude oil through distillation and subsequent determination of the fractions' a) molecular weight (MW) using atmospheric pressure photo ionization time-of-flight mass spectrometry (APPI TOF-MS) and b) GPC-RTI.

Specifically, the crude oil was separated into 27 fractions, of which the average molecular weight of each fraction was determined as its weighted average molecular weight, determined using an APPI model Time of Flight mass spectrometer (TOF-MS). Note that other mass spectrometers could be used instead. However, a TOF mass spectrometer is ideally suited for this invention, because this particular instrument type produces the most accurate molecular weight distribution. Other instrument types are based on mass analyzers with inherently greater molecular weight-biases, causing much more inaccuracy in the data for our application. Therefore, a TOF-MS is the preferred instrument for this invention.

Figure 3:
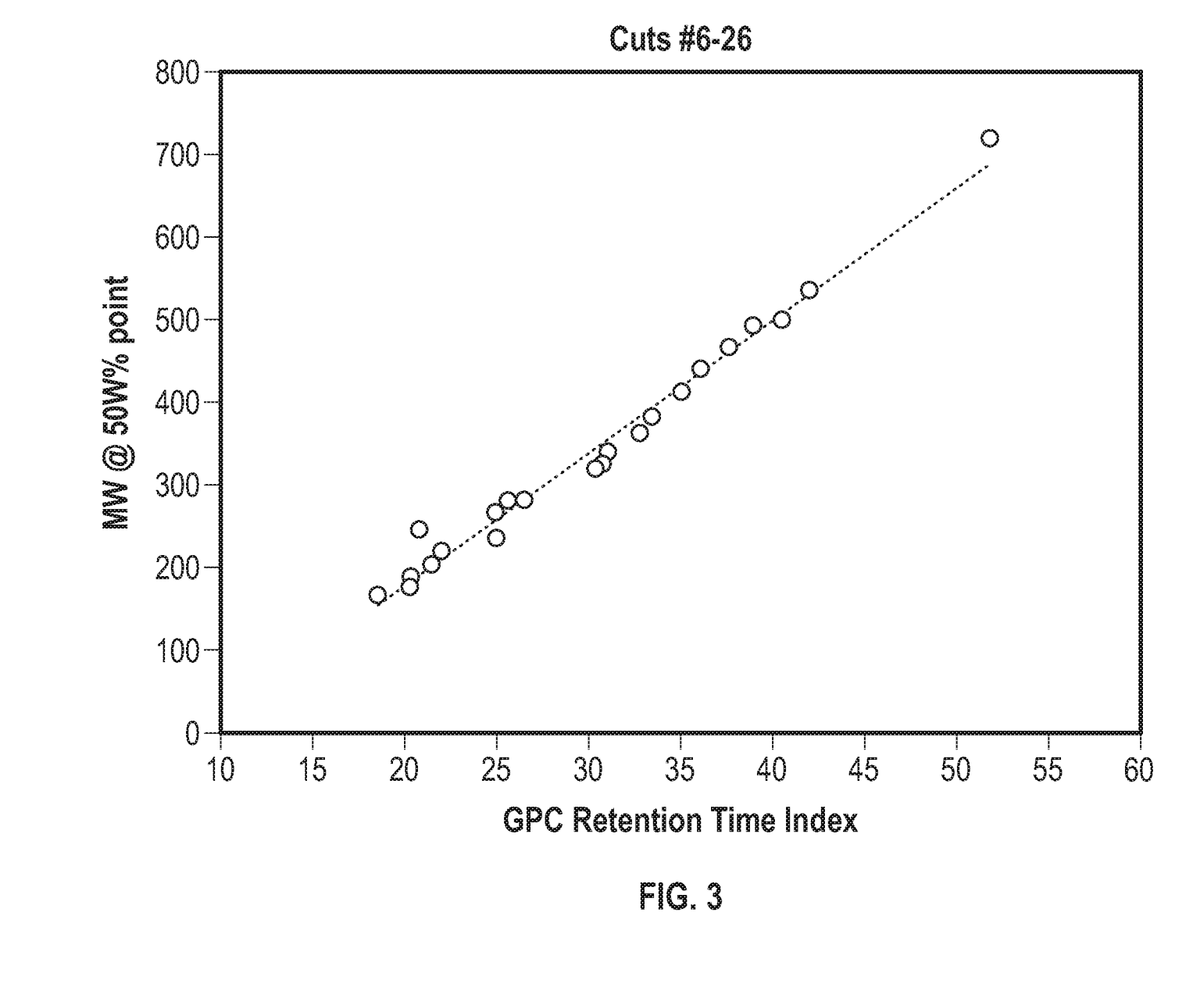
FIG. 3 is a plot of a correlation of the GPC-RTI vs. the average molecular weight (MW at 50% point) of crude oil fractions.

For this purpose, the mass spectral abundances of all mass signals measured in the fraction were summed from low mass-to-charge ratio to high mass-to-charge ratio; the mass-to-charge ratio reflecting 50% of the cumulative mass spectral abundance was considered as the average MW of the fraction. Analogously, the GPC-RTI of each fraction was determined using equation (2) as the GPC-RTI at which cumulative 50% of the fraction had eluted from the GPC apparatus. The resulting correlation is shown in FIG. 3.

In step 240, the GPC index (GPCI) is calculated as per the equation 4:

$$GPCI = \sum_{MW=150\,g/gmol}^{900\,g/gmol} GPC\ peak\ INTENSITY * MW / 1.000 \quad (4)$$

GPC PEAK Intensity=intensity value of the crude oil sample obtained at each retention time.

The correlation of GPC-RTI with the boiling point was obtained using the fractions of the crude oil (as discussed above) and subsequent determination of the fractions' a) simulated distillation profile (SIMDIS) and b) GPC-RTI.

For this purpose, the SIMDIS abundance was summed from low boiling to high boiling; the atmospheric equivalent boiling point (AEBP) reflecting 50% of the cumulative mass elution from the SIMDIS apparatus was considered as the average boiling point of the fraction. The GPC-RTI of each fraction has been explained above. The resulting correlation is shown in FIG. 3.

Steps 250 through 290 involve the calculation of the cetane number, pour point, cloud point, aniline point, and octane number, which are determined as shown in equations (5) through (9), as a function of the density and GPC index of crude oils.

$$\text{Cetane Number(CET)} = K_{CET} + X1_{CET}*\text{DEN} + X2_{CET}*(\text{DEN})^2 + X3_{CET}*(\text{DEN})^3 + X4_{CET}*\text{GPCI} + X5_{CET}*(\text{GPCI})^2 + X6_{CET}*(\text{GPCI})^3 + X7_{CET}*\text{DEN}*\text{GPCI} \quad (5)$$

$$\text{Pour Point(PP)} = K_{PP} + X1_{PP}*\text{DEN} + X2_{PP}*(\text{DEN})^2 + X3_{PP}*(\text{DEN})^3 + X4_{PP}*\text{GPCI} + X5_{PP}*(\text{GPCI})^2 + X6_{PP}*(\text{GPCI})^3 + X7_{PP}*\text{DEN}*\text{GPCI} \quad (6)$$

$$\text{Cloud Point(CP)} = K_{CP} + X1_{CP}*\text{DEN} + X2_{CP}*(\text{DEN})^2 + X3_{CP}*(\text{DEN})^3 + X4_{CP}*\text{GPCI} + X5_{CP}*(\text{GPCI})^2 + X6_{CP}*(\text{GPCI})^3 + X7_{CP}*\text{DEN}*\text{GPCI} \quad (7)$$

$$\text{Aniline Point(AP)} = K_{AP} + X1_{AP}*\text{DEN} + X2_{AP}*(\text{DEN})^2 + X3_{AP}*(\text{DEN})^3 + X4_{AP}*\text{GPCI} + X5_{AP}*(\text{GPCI})^2 + X6_{AP}*(\text{GPCI})^3 + X7_{AP}*\text{DEN}*\text{GPCI} \quad (8)$$

$$\text{Octane Number(ON)} = K_{ON} + X1_{ON}*\text{DEN} + X2_{ON}*(\text{DEN})^2 + X3_{ON}*(\text{DEN})^3 + X4_{ON}*\text{GPCI} + X5_{ON}*(\text{GPCI})^2 + X6_{ON}*(\text{GPCI})^3 + X7_{ON}*\text{DEN}*\text{GPCI} \quad (9)$$

where:

DEN=density of the crude oil sample;

GPCI=Gel permeation chromatography index of a crude oil (derived from the gel permeation chromatograpy of crude oils);

and $K_{CET}$, $X1_{CET}$-$X7_{CET}$, $K_{PP}$, $X1_{PP}$-$X7_{PP}$, $K_{CP}$, $X1_{CP}$-$X7_{CP}$, $K_{AP}$, $X1_{AP}$-$X7_{AP}$, $K_{ON}$, and $X1_{ON}$-$X7_{ON}$ are constants.

Figure 4:
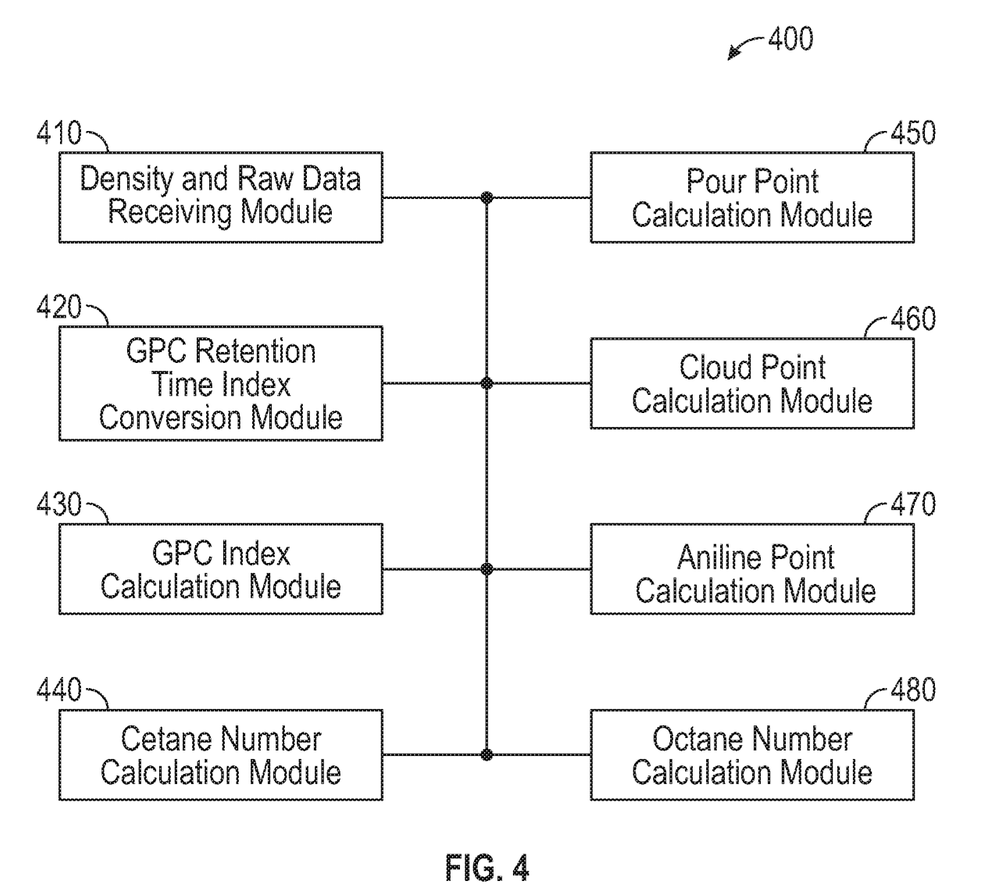
FIG. 4 is a schematic block diagram of modules of an embodiment of the invention.

FIG. 4 illustrates a schematic block diagram of modules in accordance with an embodiment of the present invention, system 400. Density and raw data receiving module 410 receives the density of a sample of crude oil and gel permeation chromatography data derived from the crude oil.

GPC retention time index conversion module 420 converts the GPC retention times from the gel permeation chromatography data to a GPC retention time index GPC-RTI, and converts that to molecular weight.

Gel permeation chromatography index calculation module 430 calculates a GPC index from the gel permeation chromatography data and the molecular weight.

Cetane number calculation module 440 derives the cetane number for the gas oil fraction of the crude oil as a function of the gel permeation chromatography index and density of the sample.

Pour point calculation module 450 derives the pour point for the gas oil fraction of the crude oil as a function of the gel permeation chromatography index and density of the sample.

Cloud point calculation module 460 derives the cloud point for the gas oil fraction of the crude oil as a function of the gel permeation chromatography index and density of the sample.

Aniline point calculation module 470 derives the aniline point for the gas oil fraction of the crude oil as a function of the gel permeation chromatography index and density of the sample.

Octane number calculation module 480 derives the octane number for the naphtha fraction of the crude oil as a function of the gel permeation chromatography index and density of the sample.

Figure 5:
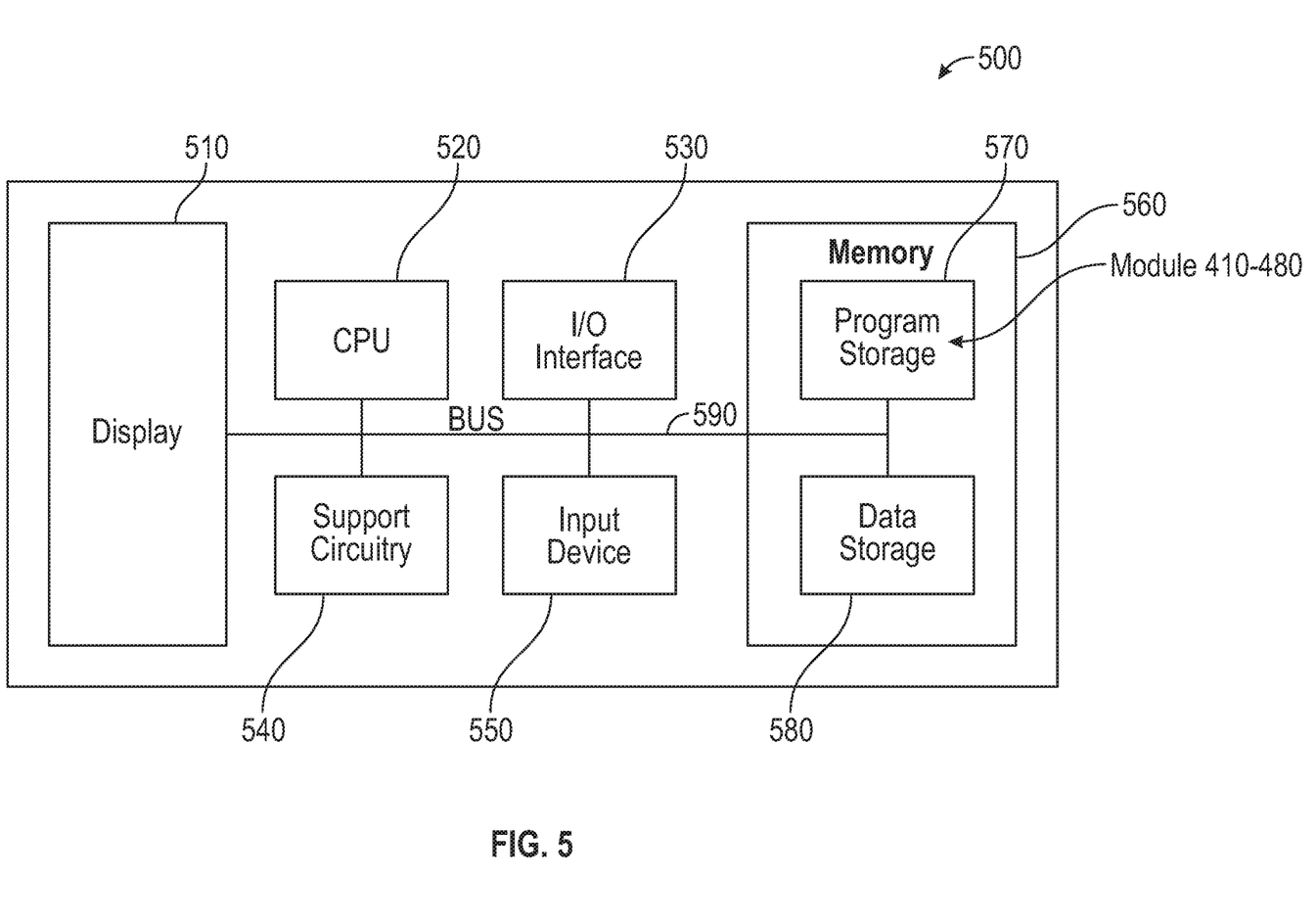
FIG. 5 is a block diagram of a computer system in which an embodiment of the invention is implemented.

FIG. 5 shows an exemplary block diagram of a computer system 500 in which one embodiment of the present invention can be implemented. Computer system 500 includes a processor 520, such as a central processing unit (CPU), an input/output interface 530 and support circuitry 540. In certain embodiments, where the computer system 500 requires a direct human interface, a display 510 and an input device 550 such as a keyboard, mouse or pointer are also provided. The display 510, input device 550, processor 520, and support circuitry 540 are shown connected to a bus 590 which also connects to a memory 560. Memory 560 includes program storage memory 570 and data storage memory 580. Note that while computer system 500 is depicted with direct human interface components display 510 and input device 550, programming of modules and exportation of data can alternatively be accomplished over the input/output interface 530, for instance, where the computer system 500 is connected to a network and the programming and display operations occur on another associated computer, or via a detachable input device as is known with respect to interfacing programmable logic controllers.

Program storage memory 570 and data storage memory 580 can each comprise volatile (RAM) and non-volatile (ROM) memory units and can also comprise hard disk and backup storage capacity, and both program storage memory 570 and data storage memory 580 can be embodied in a single memory device or separated in plural memory devices. Program storage memory 570 stores software program modules and associated data, and in particular stores a density and raw data receiving module 410, gel permeation chromatography time index conversion module 420, gel permeation chromatography index calculation module 430, cetane number calculation module 440, pour point calculation module 450, cloud point calculation module 460, aniline point calculation module 470, and octane number calculation index 480. Data storage memory 580 stores results and other data generated by the one or more modules of the present invention.

It is to be appreciated that the computer system 500 can be any computer such as a personal computer, minicomputer, workstation, mainframe, a dedicated controller such as a programmable logic controller, or a combination thereof. While the computer system 500 is shown, for illustration purposes, as a single computer unit, the system can comprise a group of computers which can be scaled depending on the processing load and database size.

Computer system 500 preferably supports an operating system, for example stored in program storage memory 570 and executed by the processor 520 from volatile memory. According to an embodiment of the invention, the operating system contains instructions for interfacing computer system 500 to the Internet and/or to private networks.

Example 1

A set of constants $K_{CET}$, $X1_{CET}$-$X7_{CET}$, $K_{PP}$, $X1_{PP}$-$X7_{PP}$, $K_{CP}$, $X1_{CP}$-$X7_{CP}$, $K_{AP}$, $X1_{AP}$-$X7_{AP}$, $K_{ON}$, and $X1_{ON}$-$X7_{ON}$ was determined using linear regression. These constants are given in Table 4.

TABLE 4

| Property | Octane Number | Cetane Number | Pour Point | Cloud Point | Aniline Point |
|---|---|---|---|---|---|
| R2 | 0.96992 | 0.93181 | 0.94898 | 0.99995 | 0.97372 |
| Constant | 1.7981E+06 | 6.9256E+04 | 7.5203E+04 | −9.2686E+04 | 4.2490E+04 |
| X1 | −6.2206E+06 | −2.4374E+05 | −2.6184E+05 | 3.3021E+05 | −1.4753E+05 |
| X2 | 7.1266E+06 | 2.8535E+05 | 3.0407E+05 | −3.7017E+05 | 1.6918E+05 |
| X3 | −2.7160E+06 | −1.1319E+05 | −1.1840E+05 | 1.3799E+05 | −6.5023E+04 |
| X4 | 2.8395E+03 | 8.3968E−04 | 2.4257E−03 | −1.3098E+03 | 1.0189E+02 |
| X5 | −1.5416E+02 | −2.2447E+01 | −8.2007E+00 | 1.0017E+02 | −1.2786E+01 |
| X6 | 4.0242E+00 | 5.2581E−01 | 2.3081E−01 | −2.6331E+00 | 3.2347E−01 |
| X7 | −1.0030E+03 | 3.5718E+02 | 1.1247E+02 | 5.1857E+01 | 7.2091E+01 |

The following example is provided to demonstrate an application of equations (5) through (9). A sample of Arabian medium crude with a 15° C./4° C. density of 0.8828 Kg/l (e.g., at 15° C./4° C. using the method described in ASTM D4052) was analyzed by gel permeation chromatography. The simulated distillation data is shown in Table 5:

TABLE 5

| RT, min | Intensity |
|---|---|
| 16 | 167.7 |
| 17 | 799.3 |
| 18 | 3304.0 |
| 19 | 4808.9 |
| 20 | 6921.1 |
| 21 | 11001.3 |
| 22 | 15268.3 |
| 23 | 18629.2 |
| 24 | 18995.1 |
| 25 | 17286.0 |
| 26 | 12536.1 |
| 27 | 8744.1 |
| 28 | 5536.6 |
| 29 | 5722.2 |
| 30 | 5630.2 |
| 31 | 1748.0 |
| 32 | 1928.1 |
| 33 | 971.9 |
| 34 | 745.8 |
| 35 | 628.1 |
| 36 | 568.4 |
| 37 | 552.1 |
| 38 | 540.9 |
| 39 | 529.3 |
| 40 | 519.5 |
| 41 | 496.5 |
| 42 | 509.2 |
| 43 | 2403.6 |
| 44 | 15209.8 |
| 45 | 49662.1 |

The GPC Index (GPCI) is calculated as 12.7372947. The calculations below are shown with GPCI and using a density at 15° C./4° C. using the method described in ASTM D4052.

Applying equation 5-9 and the constants from Table 4:

Cetane Number $(CET) =$ $K_{CET} + X1_{CET} * DEN + X2_{CET} * DEN^2 + X3_{CET} * DEN^3 + X4_{CET} * GPCI + X5_{CET} * GPCI^2 + X6_{CET} * GPCI^3 + X7_{CET} * DEN * GPCI =$ $69256.409833342 + (-243740.619543556)(0.8828) +$ $(285346.664311171)(0.8828)^2 + (-113189.503217472)(0.8828)^3 +$ $(0.000839680658405656)(12.7372947) + (-22.4465430972547)$ $(12.7372947)^2 + (0.525805574007138)(12.7372947)^3 +$ $(357.180577427041)(0.8828)(12.7372947) = 50$ Pour Point $(PP) = K_{PP} + X1_{PP} * DEN + X2_{PP} * DEN^2 +$ $X3_{PP} * DEN^3 + X4_{PP} * GPCI + X5_{PP} * GPCI^2 +$ $X6_{PP} * GPCI^3 + X7_{PP} * DEN * GPCI =$ $75202.5149915434 + (-261840.764520638)(0.8828) +$ $(304066.311141358)(0.8828)^2 + (-118404.763129288)(0.8828)^3 +$ $(0.00242573738891353)(12.7372947) + (-8.20065497159735)$ $(12.7372947)^2 + (0.230811100432963)(12.7372947)^3 +$ $(112.466857239735)(0.8828)(12.7372947) = -32$ Cloud Point $(CP) = K_{CP} + X1_{CP} * DEN + X2_{CP} * DEN^2 +$ $X3_{CP} * DEN^3 + X4_{CP} * GPCI + X5_{CP} * GPCI^2 +$ $X6_{CP} * GPCI^3 + X7_{CP} * DEN * GPCI =$ $-92685.7279442684 + (330211.516264532)(0.8828) +$ $(-370165.434577929)(0.8828)^2 + (137993.497830221)(0.8828)^3 +$ $(-1309.84137660052)(12.7372947) + (100.166943029282)$ $(12.7372947)^2 + (-2.6330608835877)(12.7372947)^3 +$ $(51.8572957053844)(0.8828)(12.7372947) = -10$ Aniline Point $(AP) = K_{AP} + X1_{AP} * DEN + X2_{AP} * DEN^2 +$ $X3_{AP} * DEN^3 + X4_{AP} * GPCI + X5_{AP} * GPCI^2 +$ $X6_{AP} * GPCI^3 + X7_{AP} * DEN * GPCI =$ $42489.9165102626 + (-147530.696443407)(0.8828) +$ $(169180.509931017)(0.8828)^2 +$ $(-65022.7396243008)(0.8828)^3 +$ $(101.888268143713)(12.7372947) + (-12.7864135323963)$ $(12.7372947)^2 + (0.323472744932636)(12.7372947)^3 +$ $(72.0908287913078)(0.8828)(12.7372947) = 65$ Octane Number $(ON) = K_{ON} + X1_{ON} * DEN + X2_{ON} * DEN^2 +$ $X3_{ON} * DEN^3 + X4_{ON} * GPCI + X5_{ON} * GPCI^2 +$ $X6_{ON} * GPCI^3 + X7_{ON} * DEN * GPCI =$ $1798073.87068223 + (-6220639.79247671)(0.8828) +$ $(7126551.8554278)(0.8828)^2 + (-2716014.65577734)(0.8828)^3 +$ -continued $$(2839.54396874223)(12.7372947) + (-154.160799835634)$$
$$(12.7372947)^2 + (4.02420839644695)(12.7372947)^3 +$$
$$(-1003.01822106596)(0.8828)(12.7372947) = 53$$

Accordingly, as shown in the above example, indicative properties including cetane number, pour point, cloud point, aniline point, and octane number can be assigned to the crude oil samples without fractionation/distillation (crude oil assays).

In alternate embodiments, the present invention can be implemented as a computer program product for use with a computerized computing system. Those skilled in the art will readily appreciate that programs defining the functions of the present invention can be written in any appropriate programming language and delivered to a computer in any form, including but not limited to: (a) information permanently stored on non-writeable storage media (e.g., read-only memory devices such as ROMs or CD-ROM disks); (b) information alterably stored on writeable storage media (e.g., floppy disks and hard drives); and/or (c) information conveyed to a computer through communication media, such as a local area network, a telephone network, or a public network such as the Internet. When carrying computer readable instructions that implement the present invention methods, such computer readable media represent alternate embodiments of the present invention.

As generally illustrated herein, the system embodiments can incorporate a variety of computer readable media that comprise a computer usable medium having computer readable code means embodied therein. One skilled in the art will recognize that the software associated with the various processes described can be embodied in a wide variety of computer accessible media from which the software is loaded and activated. Pursuant to In re Beauregard, 35 U.S.P.Q.2d 1383 (U.S. Pat. No. 5,710,578), the present invention contemplates and includes this type of computer readable media within the scope of the invention. In certain embodiments, pursuant to In re Nuuten, 500 F.3d 1346 (Fed. Cir. 2007) (U.S. patent application Ser. No. 09/211,928), the scope of the present claims is limited to computer readable media, wherein the media is both tangible and non-transitory.

The system and method of the present invention have been described above and with reference to the attached figures; however, modifications will be apparent to those of ordinary skill in the art and the scope of protection for the invention is to be defined by the claims that follow.

We claim:

1. A system for evaluating a crude oil sample and calculating an indicative property of a naphtha or gas oil fraction of the crude oil sample without first distilling said naphtha or gas oil fraction, the system comprising:
   a high performance liquid chromatograph that analyzes the crude oil sample for gel permeation chromatography (GPC) analysis;
   a non-volatile memory device that stores calculation modules and data, the data including density of the crude oil sample and gel permeation chromatography data indicative of GPC peak intensity, full permeation time, retention time, and full exclusion time at predetermined increments between a predetermined range for the oil sample, as derived by an analysis of the crude oil sample by the high performance liquid chromatograph;
   a processor coupled to the non-volatile memory;
   a first calculation module that, when executed by the processor, calculates GPC retention time index as a function of the full permeation time, retention time, and full exclusion time, and enters the GPC retention time index into the non-volatile memory;
   a second calculation module that, when executed by the processor, converts the GPC retention time index to molecular weight, and enters the molecular weight into the non-volatile memory;
   a third calculation module that, when executed by the processor, calculates and enters into the non-volatile memory a GPC index as the sum of the products of GPC peak intensity and molecular weight over a range of molecular weights;
   a fourth calculation module that calculates the indicative property for the naphtha or gas oil fraction of the crude oil from a two-variable polynomial equation with predetermined constant coefficients developed using linear regression techniques, and that stores the indicative property into the non-volatile memory device;
   wherein the two variables of the two-variable polynomial equation are the GPC peak intensity and the density of the crude oil sample.

2. The system of claim 1, wherein the indicative property is the cetane number.

3. The system of claim 1, wherein the indicative property is the pour point.

4. The system of claim 1, wherein the indicative property is the cloud point.

5. The system of claim 1, wherein the indicative property is the aniline point.

6. The system of claim 1, wherein the indicative property is the octane number.

7. The system of claim 1, wherein the range of molecular weights is 150 g/gmol to 900 g/gmol.

8. A method for evaluating a crude oil sample and calculating an indicative property of a naphtha or gas oil fraction of the crude oil sample without first distilling said naphtha or gas oil fraction, the method comprising:
   obtaining density of the crude oil sample;
   subjecting said crude oil sample to gel permeation chromatography (GPC) analysis, and entering GPC peak intensity, full permeation time, retention time, and full exclusion time determined by the GPC analysis into non-volatile memory of a computer;
   using a processor of the computer and enter into the non-volatile memory to calculate a GPC retention time index as a function of the full permeation time, retention time, and full exclusion time;
   using the processor to convert the GPC retention time index to molecular weight, and to enter the molecular weight into the non-volatile memory;
   using the processor to calculate and enter into the non-volatile memory a GPC index as the sum of the products of GPC peak intensity and molecular weight over a range of molecular weights;
   and using the processor to calculate and enter into the non-volatile memory the indicative property for the naphtha or gas oil fraction of the crude oil from a two-variable polynomial equation with predetermined constant coefficients developed using linear regression techniques;
   wherein the two variables of the two-variable polynomial equation are the GPC peak intensity and the density of the crude oil sample.

9. The method of claim 8, wherein the indicative property is the cetane number.

10. The method of claim 8, wherein the indicative property is the pour point.

11. The method of claim 8, wherein the indicative property is the cloud point.

12. The method of claim 8, wherein the indicative property is the aniline point.

13. The method of claim 8, wherein the indicative property is the octane number.

14. The method of claim 8, wherein the range of molecular weights is 150 g/gmol to 900 g/gmol.

* * * * *